United States Patent [19]
Harding

[11] Patent Number: 5,176,151
[45] Date of Patent: Jan. 5, 1993

[54] ORAL PROPHYLACTICS

[76] Inventor: Glen R. Harding, P.O. Box 1281, La Jolla, Calif. 92038

[21] Appl. No.: 702,181

[22] Filed: May 20, 1991

Related U.S. Application Data

[63] Continuation-in-part of Ser. No. 89,780, Aug. 27, 1987, Pat. No. 4,949,731.

[51] Int. Cl.⁵ .......................... A61F 6/02; A61B 1/24
[52] U.S. Cl. ...................................... 128/842; 128/15
[58] Field of Search ................... 606/918, 79, 15, 193, 606/194; 604/330, 347–353; 128/830–861; 424/424, 425, 431, 432

[56] References Cited

U.S. PATENT DOCUMENTS

| | | | |
|---|---|---|---|
| 2,614,047 | 10/1952 | Turner | 426/91 |
| 3,062,662 | 11/1962 | McDonald | 426/91 |
| 3,477,394 | 11/1969 | Tidwell | 426/91 |
| 3,867,927 | 2/1975 | Hergott | 128/15 |
| 3,950,548 | 4/1976 | Baker | 426/91 |
| 4,430,075 | 2/1984 | Urban | 604/77 |
| 4,520,809 | 6/1985 | de Greef | 128/200.24 |
| 4,581,013 | 4/1986 | Allen | 604/78 |
| 4,902,519 | 2/1990 | Ream | 426/91 |
| 4,919,149 | 4/1990 | Stang | 128/844 |

Primary Examiner—Michael A. Brown

[57] ABSTRACT

A resilient and flexible intra-oral device which control releases pharmaceutical preparations into the mouth. A preferred embodiment of the device is a silicone lollipop.

8 Claims, 1 Drawing Sheet

5,176,151

ORAL PROPHYLACTICS

This application is a continuation-in-part of Ser. No. 07/089,780, filed Aug. 27, 1987 now U.S. Pat. No. 4,949,731.

FIELD OF THE INVENTION

This invention relates generally to the field of oral prophylaxis, and more particularly to an intra-oral device which control releases pharmaceutical preparations into the mouth. Example preparations include flavor essences, herbal remedies, and ethical drugs, particularly those drugs targeted for systemic absorption across the oral mucosa, or those targeted for local delivery to the mouth and throat. The preferred device embodiment is a lollipop fabricated in silicone elastomer.

A problem addressed by the present invention is the lack of effective oral therapy. Many people instead smoke or overeat to appease neuroses. The present invention is therefore related to cigarettes, pacifiers, and the like since they provide a form of oral satisfaction, and are easy to use.

A further problem is the lack of effective control release delivery of therapeutic agents into the mouth for systemic absorption across the oral mucosa, or local treatment of the mouth and throat. The present invention is therefore related to lozenges, chewing gum, buccal tablets, and the like since they release pharmaceutical preparations into the mouth.

In view of the foregoing factors, it is a primary objective of the present invention to provide a novel intraoral device which is resilient, flexible, and orally satisfying.

Another objective of the present invention is providing an intra-oral device that is safe, unobtrusive, and easy to use.

Still another objective of the present invention is providing a control release lollipop that is durable and has tactile means applied to the insert and handle portions.

Still a further objective of the present invention is providing an intra-oral device that incorporates non-toxic colors.

And still a further objective of the present invention is providing an intra-oral device that is flavorful and sustains the duration of its flavor potency.

Another primary objective of the present invention is providing an intra-oral device which control releases flavor essences, vitamins, herbal remedies, and the like, into the mouth.

Another objective of the present invention is providing an intra-oral device that control releases an ethical drug into the oral cavity for the purpose of systemic absorption into a user's bloodstream.

Still another objective of the present invention is providing an intra-oral device that control releases an ethical drug into the oral cavity for the purpose of local, topical therapies of the mouth and throat.

SUMMARY

The intra-oral device includes a resilient flexible body construction having an insert portion that is received into the mouth over the tongue, and further having a handle portion that is maintained outside of the mouth. Furthermore, the device includes embodiments wherein a pharmaceutical preparation is mixed into a liquid silicone elastomer and then cure-hardened for the purpose of control releasing the embedded preparation into a user's mouth.

DRAWINGS

DESCRIPTION

According to a preferred embodiment of the present invention, the intra-oral device includes a handle portion maintained outside of the mouth and an insert portion received into the mouth.

Figure 1:
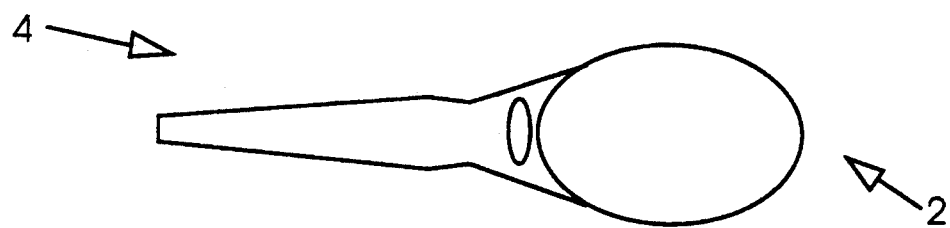
FIG. 1 is a plan view of an embodiment of the intra-oral device showing an elongated handle portion 4 and an elliptical insert portion 2.

Referring now to the drawings and particularly FIG. 1, a control release lollipop is shown having a tubular handle portion 4, and an elliptical insert portion 2. The handle portion 4 is adapted for handling the device with the hand, and is also adapted to a user's lips while the lollipop is in the user's mouth. The insert portion 2 is adapted for being inside of a user's mouth and therefore must accomodate the user's tongue, palate, and teeth.

One preferred embodiment of the present invention is fabricated in a unitary construction in silicone elastomer. A pharmaceutical preparation, a flavor essence for example, is first mixed into a liquid silicone and then this silicone and flavor dispersion is cure-hardened into the shape of a lollipop. In this unitary construction, the handle and insert portions of the lollipop both contain the embedded flavoring. Moreover, non-toxic coloring may be added to the liquid silicone before cure-hardening the device. A preferred manufacturing method is liquid injection molding.

Since silicone is permeable, saliva in the mouth permeates it at a controlled rate. This rate is affected by the surface area of the cured device, which may be increased by adding holes, and factors such as adding release enhancers and retardants to the liquid silicone elastomer before curing it. If a soluble pharmaceutical preparation is cured into the control release lollipop, it will dissolve out of the cured silicone elastomer matrix as saliva permeates it, if a non soluble pharmaceutical preparation is desired, it may be formulated with a soluble filler, or with an erodable silicone and applied as an outer layer to the insert portion. Another embodiment of the control release lollipop is fabricated in a two part system. In this case only the insert portion incorporates a pharmaceutical preparation for control release into the mouth. In a preferred manufacturing method, the lollipop is first molded as a unitary device in a durable silicone elastomer. A pharmaceutical preparation is then formulated into a second silicone which is applied, by dipping, spraying, or double liquid injection molding, as an outer layer of only the insert portion.

Still another embodiment of the control release lollipop is fabricated in a two part system wherein the insert portion is mechanically bonded to the handle portion. In a preferred embodiment, the end of the handle portion which connects to the insert portion is flattened into a disk shape and has a pattern of holes cut through it. The insert portion, a liquid silicone formulated for control release, is then molded around and through the holes and mechanically bonds to the handle portion. Moreover, the handle portion could be fabricated in a flexible plastic material, such as Teflon, and furthermore, the handle and insert portions could be joined together using a mechanical clasp.

The materials and shapes herein specified are examples and many ones may be substituted. Accordingly, it is intended that the foregoing disclosure be considered only as illustration of principles of the invention.

A primary purpose of the present invention is providing oral satisfaction. The intra-oral device is durable and remains intact throughout its use in the mouth. Furthermore, the device sustains its flavor potency, and is resilient to biting and sucking. Moreover, the insert portion of the lollipop may be textured to enhance its tactile sensation to the mouth, and the handle portion may be textured for sensation to the hand. A ball, or like attachment on the end of the handle portion remote from the insert portion, also facilitates nervous handling of the lollipop.

Another primary purpose of the control release lollipop is providing control release delivery of therapeutic agents across the oral mucosa of a user's mouth. This delivery method offers potential benefits since the drug would enter directly into a user's systemic circulation and thereby avoid gastrointestinal and liver metabolism. An example drug targeted for systemic delivery across the oral mucosa is benzodiazapene, a medication administered to children before operations. Another example systemic drug is nicotine. Furthermore, the lollipops may have non-toxic means for changing color after the control release preparation has completely dissolved from the silicone elastomer matrix.

Still another primary purpose of the present invention is providing control release delivery of therapeutic agents for local, topical treatments of the mouth and throat. In the embodiment of a control release lollipop, the intra-oral device is unembarassing and easy to use, and provide direct application to the mouth and throat. An example topical drug preparation is benzocaine and menthol which together are used as a local anesthetic to relieve sore throats.

Figure 2:
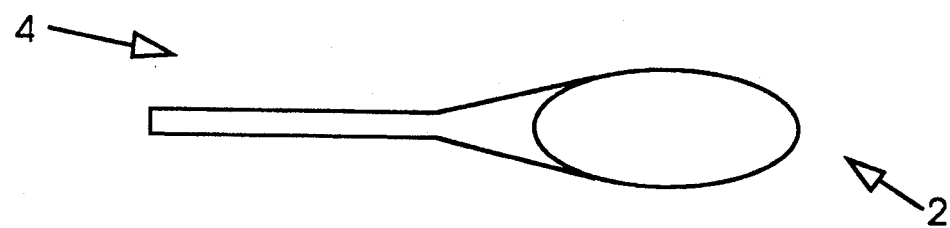
FIG. 2 is a side view of the embodiment of FIG. 1.

Referring to FIGS. 1-2, the insert portion 2 is received into the mouth above the tongue of a user, and the handle portion 4 is maintained outside of the mouth. The insert portion 2 primarily functions as a means for control releasing pharmaceutical preparations into the mouth. A user places the insert portion into the mouth and saliva permeates the silicone and dissolves out any soluble preparation that was mixed and then cured into the silicone matrix. Alternatively, the insert portion could be constructed using a release rate controlling membrane and reservoir, instead of matrix, control release technology. The handle portion 4 primarily facilitates handling and guards against swallowing the device. Moreover, a mechanical clip may be added to the end of the handle portion remote from the insert portion to secure the device to a patient's shirt.

Although the present invention has been described with reference to certain embodiments, other versions are possible. For example, the shapes and cross-sections of the handle and insert portions may readily be changed. By vanishing the insert portion, a tubular, cigarette shaped intra-oral device is formed. By vanishing the handle portion and hollowing and enlarging the remaining insert portion, an elliptical, teething ring shaped intra-oral device is formed. Other materials for the oral environment and having controlled release properties may be substituted. Moreover, the intra-oral device may be constructed as a unitary or a two-piece system. Therefore, the spirit and scope of the appended claims should not be limited to description of the versions contained herein.

I claim:

1. A control release lollipop for use in the mouth and adapted for the lips of a wearer comprising:

a flexible, resilient and unitary body having an insert portion received into the mouth above the tongue of the wearer, wherein said insert portion is substantially elliptical and adapted for the oral cavity, and having a handle portion connected to said insert portion, wherein said handle portion extends outside of the mouth of the wearer, wherein said handle portion is substantially tubular; and wherein said unitary body is a silicone elastomer; and wherein said silicone elastomer is mixed, while in a liquid state, with a pharmaceutical preparation selected from the group consisting of natural plant and fruit flavors, and synthetic pharmacological compounds; and wherein said liquid silicone and pharmaceutical preparation mixture is liquid injection molded.

2. The control release lollipop according to claim 1 wherein at least part of said insert and handle portions has texture means selected from the group consisting of ribs, holes, dimples, setae, and striation grids.

3. The control release lollipop according to claim 1 further having non-toxic coloring means which is added to said liquid silicone prior to said liquid injection molding.

4. A control release lollipop for use in the mouth and adapted for the lips of a wearer comprising:

a flexible, two part system having an insert portion as a first part received into the mouth above the tongue of the wearer, wherein said insert portion is substantially elliptical and adapted for the oral cavity, and having a handle portion as a second part connected to said insert portion, wherein said handle portion extends outside of the mouth of the wearer, wherein said handle portion is substantially tubular; and wherein at least part of the construction material of said insert portion is a silicone elastomer; and wherein said silicone elastomer is mixed, while in a liquid state, with a pharmaceutical preparation selected from the group consisting of natural plant and fruit flavors, and synthetic pharmacological compounds.

5. The control release lollipop according to claim 4 wherein at least part of said insert and handle portions has texture means selected from the group consisting of ribs, holes, dimples, setae, and striation grids.

6. The control release lollipop according to claim 4 wherein said insert and handle portions are first molded as a unitary body in a first, durable silicone, and wherein a second silicone is mixed, while in a liquid state, with said pharmaceutical preparation, and then applied as an outer layer to only the said insert portion.

7. The second, outer layer of silicone according to claim 6 wherein said silicone is room temperature vulcanizing and applied to only the said insert portion by either dipping or spraying.

8. The control release lollipop according to claim 4 wherein said handle portion is a thermoset plastic.

* * * * *